United States Patent [19]
Hirano et al.

[11] Patent Number: 5,634,922
[45] Date of Patent: Jun. 3, 1997

[54] CANCER DIAGNOSIS AND TREATMENT DEVICE HAVING LASER BEAM GENERATOR

[75] Inventors: Toru Hirano; Hideo Suzuki, both of Hamamatsu, Japan

[73] Assignee: Hamamatsu Photonics K.K., Shizuoka-ken, Japan

[21] Appl. No.: 368,769

[22] Filed: Jan. 4, 1995

Related U.S. Application Data

[63] Continuation of Ser. No. 616,048, Nov. 20, 1990.

[30] Foreign Application Priority Data

| Nov. 20, 1989 | [JP] | Japan | 1-301783 |
| Feb. 9, 1990 | [JP] | Japan | 2-30757 |

[51] Int. Cl.$^6$ ..................................... A61N 5/06
[52] U.S. Cl. ..................... 606/10; 606/3; 606/7; 606/12; 606/15; 607/88; 607/89
[58] Field of Search .................. 607/88–95; 606/3–7, 606/10–18; 359/330

[56] References Cited

U.S. PATENT DOCUMENTS

| 3,487,835 | 1/1970 | Koester et al. ............................... 606/4 |
| 3,609,389 | 9/1971 | Bjorkholen ................................. 359/330 |
| 4,266,549 | 5/1981 | Kimura . | |

(List continued on next page.)

FOREIGN PATENT DOCUMENTS

| 3301092 | 8/1983 | Germany . |
| 63-23648 | 1/1988 | Japan . |
| 1151436 | 6/1989 | Japan . |
| 2125986 | 3/1984 | United Kingdom . |
| 2125986B | 3/1984 | United Kingdom . |
| 8700748 | 12/1987 | WIPO .................................. 606/5 |

OTHER PUBLICATIONS

Medical Physics, vol. 13, No. 5, Sep./Oct. 1986, *Digital background subtraction for fluorescence imaging*, pp. 717–721, A. Edward Profio et al.

Applied Spectroscopy, vol. 38, No. 6, 1984, *Laser–Induced Fluorescence Studies of Hematoporphyrin Derivative HPD in Normal and Tumor Tissue of Rat*, pp. 890–896, J. Ankerst et al.

Reprints from Harwood Academic Publishers, (Received Jun. 10, 1989), *Photodynamic Cancer Diagnosis and Treatment System Consisting of Pulse Lasers and an Endoscopic Spectro–Image Analyzer*, pp. 99–116, T. Hirano et al.

University and Science, Jan. 27, 1989, *High Technology for Supporting Medical Treatment*, pp. 324–332.

*Primary Examiner*—David M. Shay
*Attorney, Agent, or Firm*—Sughrue, Mion, Zinn, Macpeak & Seas

[57] ABSTRACT

A cancer diagnosis and treatment device comprising a solid-state laser generator such as an Nd-YAG laser, an alexandrite laser, or titanium sapphire laser for emitting a first laser beam having a first wavelength, a harmonic generator for generating higher harmonic laser beams of the first laser beam and outputting one of the higher harmonic laser beams, and an optical parametric oscillator for converting the harmonic laser beam outputted from the harmonic generator into second and third laser beams suitable for the cancer diagnosis and treatment, the second laser beam having a second wavelength stimulating a sterilizing photochemical reaction between the photosensitive material and the cancer foci to perform the cancer treatment and the third laser beam having a third wavelength inducing fluorescence inherent to the photosensitive material to enable the cancer diagnosis, an endoscope for guiding the second and third laser beams emitted from the laser beam source to the cancer foci and transmitting an image of the fluorescence of the photosensitive material to an outside of the body, and a cancer observing unit having a screen for receiving the image of the fluorescence of the photosensitive material al transmitted through the endoscope unit and displaying the image on the screen to thereby perform the cancer diagnosis.

17 Claims, 4 Drawing Sheets

U.S. PATENT DOCUMENTS

| | | | |
|---|---|---|---|
| 4,336,809 | 6/1982 | Clark | 606/3 |
| 4,395,397 | 7/1983 | Shapiro . | |
| 4,538,608 | 9/1985 | L'Esperance | 606/10 |
| 4,556,057 | 12/1985 | Hiruma et al. | 606/14 |
| 4,639,923 | 1/1987 | Tang et al. | 359/330 |
| 4,768,513 | 9/1988 | Suzuki | 606/9 |
| 4,785,806 | 11/1988 | Deckelbaum | 372/23 |
| 4,791,927 | 12/1988 | Merger | 606/3 |
| 4,866,720 | 9/1989 | Holly | 606/7 |
| 5,066,291 | 11/1991 | Stewart | 606/3 |
| 5,071,416 | 12/1991 | Heller et al. | 606/3 |

CANCER DIAGNOSIS AND TREATMENT DEVICE HAVING LASER BEAM GENERATOR

This is a Continuation of application Ser. No. 07/616,048 filed Nov. 20, 1990.

BACKGROUND OF THE INVENTION

This invention relates to a cancer diagnosis and treatment device, and more particularly to a cancer diagnosis and treatment device for simultaneously performing cancer diagnosis and treatment with laser beams having different wavelengths suitable for cancer diagnosis and treatment.

There has been developed a cancer diagnosis and treatment system for simultaneously performing diagnosis and treatment of a malignant tumor such cancer using laser beams having different wavelengths. In this system, a photosensitive material such as hematoporphyrin derivative (HpD), dihematoporphyrin ether/ester (DHE) Or the like, which has affinity to cancer foci and fluorescent characteristic, is beforehand injected through a vein of a patient so that the photosensitive material is selectively absorbed in the cancer foci, and then two kinds of laser beams having different wavelengths are irradiated to the cancer foci to perform diagnosis and treatment of the cancer. The photosensitive material, for example, HpD emits characteristic red fluorescence with two peaks at 630 and 690 nm when exposed to light of an appropriate exciting wavelength (405 nm), and thus a diagnosis of cancer is performed by detecting the fluorescence of HpD. On the other hand, HpD is excited into its excited state when exposed to light of 630 nm, and then its exciting energy is transferred to an oxygen ($O_2$) within the body of the patient to excite and activate the oxygen, and the activated oxygen acts on the cancer focus and destroys it. Accordingly, the cancer diagnosis and treatment can be performed using a photosensitive material and two laser beams having different wavelengths located in an absorption spectral range of the photosensitive material.

Figure 1:
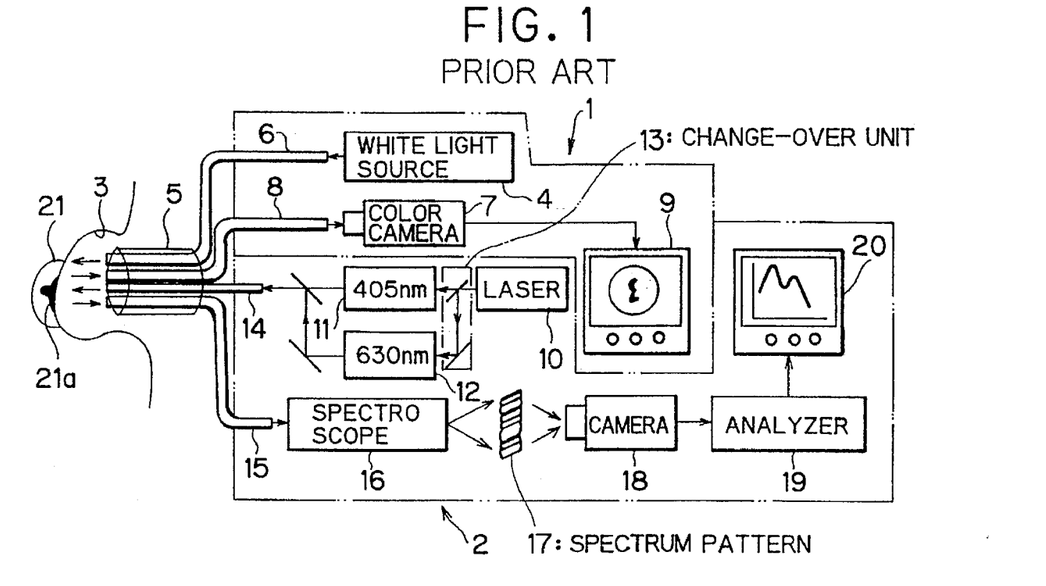
FIG. 1 shows a conventional cancer diagnosis and treatment device.

FIG. 1 shows a conventional cancer diagnosis and treatment device comprising an ordinary endoscopic diagnosis system 1 for observing a malignant tissue 21 having cancer focus 21a with an endoscope 5, and an optical diagnosis and treatment system 2 for performing cancer diagnosis and treatment of the tissue through fluorescence of the photosensitive material and through a sterilizing photochemical reaction between the injected photosensitive material and cancer foci. The endoscopic diagnosis system 1 includes a light source 4 for irradiating a white light to the surface of the tissue 21 containing the cancer focus 21a to observe the malignant tissue 21, a light guide 6 of the endscope 5 for guiding the white light to the tissue 21, an image guide 8 for guiding an image light of the surface of the tissue 21 to a color camera 7, and a TV monitor 9 for displaying the image obtained by the color camera 7. On the other hand, the optical diagnosis and treatment device 2 includes a laser beam generating device comprising a fundamental laser beam generator 10 for emitting a fundamental laser beam, a diagnostic laser beam generator 11 for generating a laser beam for diagnosis (for example, having a wavelength of 405 nm) using the fundamental laser beam and a treating laser beam generator 12 for generating a laser beam for treatment (for example, having a wavelength of 630 nm for HpD) using the fundamental laser beam, and a changeover unit 13 for selecting one of the laser beams of the diagnostic and treating laser beam generators 11 and 12. These laser beams for cancer diagnosis and treatment are guided through a light guide 14 to the tissue 21.

When the hematoporphyrin derivative (HpD) at pH 7.4, which is formed by dissolving hematoporphyrin hydrochloride in a mixture of sulfuric acid and acetic acid, is used for intravenous injection, upon incidence of a laser beam of 405 nm to the tissue 21 in a diagnostic procedure, fluorescence with two peaks at 630 and 690 nm is emitted from the hematoporphyrin derivative within the tissue. The fluorescence is transmitted through a light guide 15 of the endoscope 5 to a spectroscope 16 in which a spectrum pattern 17 of the fluorescence is produced. The spectrum pattern 17 thus obtained is picked up by a high-sensitive camera 18 comprising, for example, an image intensifier and a silicon intensified target (SIT) camera to obtain a video signal of the spectrum pattern 17. The video signal outputted from the high-sensitive camera 18 is processed by an analyzer 19 to obtain a graphical spectrum image of the fluorescence, which is finally displayed on a TV monitor 20. The spectrum pattern 17 of the fluorescence has a structure having two peaks at 630 and 690 nm, which is characteristic of the fluorescence of HpD, and thus a spectroscopic range of the spectroscope 16 is set to 600 to 700 nm in wavelength. The tissue 21 having the cancer focus 21a is discriminated in the above diagnosis procedure. Thereafter, the laser beam (405 nm) for cancer diagnosis is switched to the laser beam (630 nm) for cancer treatment by the change-over unit 13, and the laser beam for cancer treatment is irradiated to only the cancer focus 21a to destroy only the cancer focus 21a.

Figure 2:
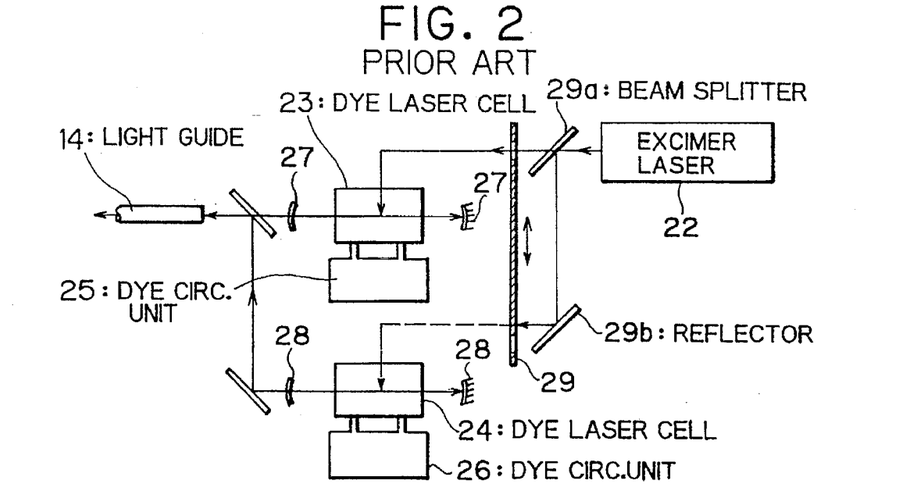
FIG. 2 shows a conventional laser beam generating device used in the cancer diagnosis and treatment device as shown in FIG. 1.

FIG. 2 shows a conventional laser beam generating device used in the cancer diagnosis and treatment device as shown in FIG. 1, and comprises an excimer laser generator 22 serving as the laser beam generator 10 for emitting a laser beam of 308 nm, and two kinds of dye laser cells 23 and 24, serving as the diagnostic and treating laser beam generators 11 and 12 as shown In FIG. 1, which are excited by the laser beam of 308 nm from the excimer laser generator 22 to output laser beams of 405 and 630 nm, respectively. The laser beam (308 nm) of the excimer laser generator 22 is split into two laser beams by a beam splitter 29a and one of the laser beams is transmitted through a change-over unit 29 to the first dye laser cell 23 while the other is reflected by a reflector 29b and transmitted through the change-over unit 29 to the second dye laser cell 24. A dye of the first dye laser cell 23 is circulated by a dye circulating unit 25 and is excited by one laser beam from the excimer laser generator 22 to output a laser beam of 405 nm using a pair of reflectors 27. On the other hand, another kind of dye of the second dye laser cell 24 is also circulated by another dye circulating unit 26 and is excited by the other laser beam from the excimer laser generator 22 to output a laser beam of 630 nm using a pair of reflectors 28. These laser beams emitted from the first and second dye laser cells 23 and 24 are guided through a light guide 14 to the cancer focus 21a.

A laser beam produced by the excimer laser generator 22 has a high pulse height and thus is effectively used for cancer diagnosis and treatment. However, since a laser gas used for the excimer laser generator 22 has a shorter life time, it is difficult to maintain a stable oscillating operation in the excimer laser generator 22 for a long time. In addition, it is required to circulate the laser gas within the excimer laser generator 22 and to exchange an used laser gas for a new one, for example, every week. As a result, the conventional laser beam generating device thus constructed has disadvantages that the construction thereof is complicated and the operation thereof is practically unstabilized.

SUMMARY OF THE INVENTION

An object of this invention is to provide a cancer diagnosis and treatment device capable of producing a laser beam having a long life time and a stable oscillating operation for cancer diagnosis and treatment.

Another object of this invention is to provide a cancer diagnosis and treatment device capable of freely changing the wavelength of a laser beam for cancer diagnosis and treatment in accordance with the kind of a photosensitive material to be injected into a human body.

In order to attain the above objects, a cancer diagnosis and treatment device according to this invention in which cancer diagnosis and treatment is performed using a photosensitive material having affinity to cancer foci in a body and laser beams having different wavelengths in an absorption wavelength range of the photosensitive material, comprises a laser beam source including a solid-state laser generator for emitting a first laser beam having a first wavelength, and a laser-wavelength varying unit for converting the first laser beam into second and third laser beams suitable for the cancer diagnosis and treatment through harmonic generation and optical parametric oscillation, the second laser beam having a second wavelength stimulating a sterilizing photochemical reaction between the photosensitive material and the cancer foci to perform the cancer treatment and the third laser beam having a third wavelength inducing fluorescence inherent to the photosensitive material to enable the cancer diagnosis, an endoscope unit for guiding the second and third laser beams emitted from the laser beam source to the cancer foci and for transmitting an image of the fluorescence of the photosensitive material to an outside of the body, and a cancer observing unit having a screen for receiving the image of the fluorescence of the photosensitive material transmitted through said endoscope unit and displaying the image on the screen to thereby perform the cancer diagnosis.

The solid-state laser generator comprises an Nd-YAG laser generator for emitting a monochromatic laser beam having wavelength of 1064 nm, or a wavelength-variable laser generator such as an alexandrite laser beam having wavelength variable over a range of 700 to 830 nm or a titanium sapphire laser generator for emitting a laser beam having wavelength variable over a range of 680 to 900 nm.

The laser-wavelength varying unit comprises a harmonic generator for generating higher harmonic laser beams of the first laser beam and an optical parametric oscillator for generating the second and third laser beams having different wavelengths suitable for cancer diagnosis and treatment. The optical parametric oscillator includes a nonlinear optical crystal for emitting the second and third laser beams having wavelengths different from that of the first laser beam, and the wavelengths of the second and third laser beams are variable by changing an incident angle of the first laser beam to the crystal, thereby freely changing the wavelengths of the second and third laser beams in accordance with the kind of the photosensitive material.

DETAILED DESCRIPTION OF THE INVENTION

Preferred embodiments of this invention will be described hereunder with reference to the accompanying drawings.

Figure 3:
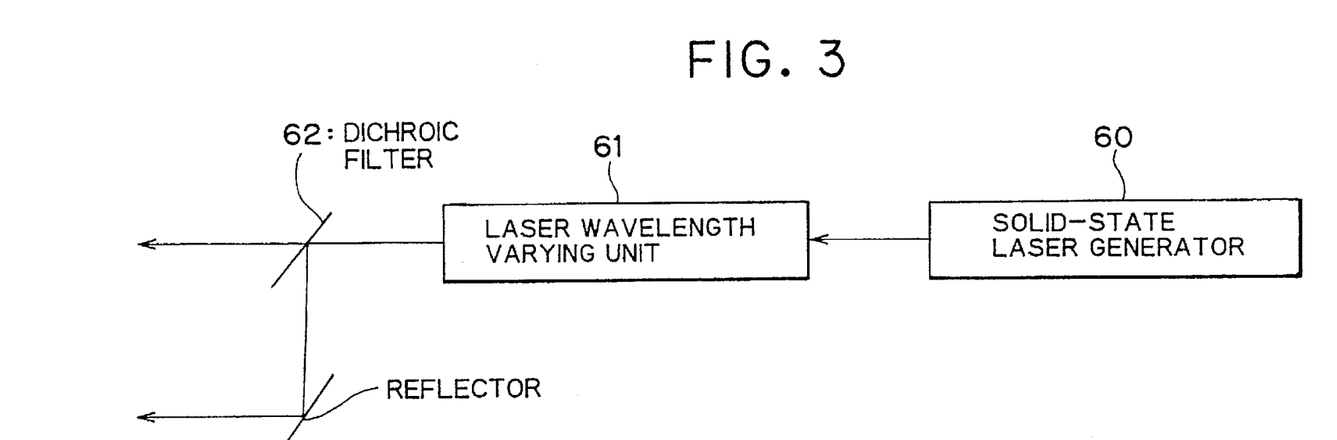
FIG. 3 shows a first embodiment of a laser beam generating device used in the cancer diagnosis and treatment device according to this invention.

FIG. 3 is a schematic view of a first embodiment of the laser beam generating device used in a cancer diagnosis and treatment device according to this invention.

As shown in FIG. 3, the laser beam generating device according to this embodiment comprises a solid-state laser generator 60 for emitting a monochromatic laser beam, a laser-wavelength varying unit 61 for converting the laser beam emitted from the solid-state laser generator 60 to two laser beams having desired wavelengths suitable for cancer diagnosis and treatment, and a dichroic filter 62 for separating the laser beams having the desired wavelengths, which are used for cancer diagnosis and treatment, respectively. In this embodiment, the solid-state laser generator 60 is substituted for the excimer laser generator used in the conventional laser beam generating device because the solid-state laser generator can carry out a more stable oscillating operation for a long time and requires no exchange of laser gas (in this point, the excimer laser generator requires exchange of laser gas). As described hereinafter, the laser-wavelength varying unit 61 may have various constructions in accordance with the kind of the solid-state laser generator 60 and/or the kind of photosensitive material to be injected into the vein of the patient.

Figure 4:
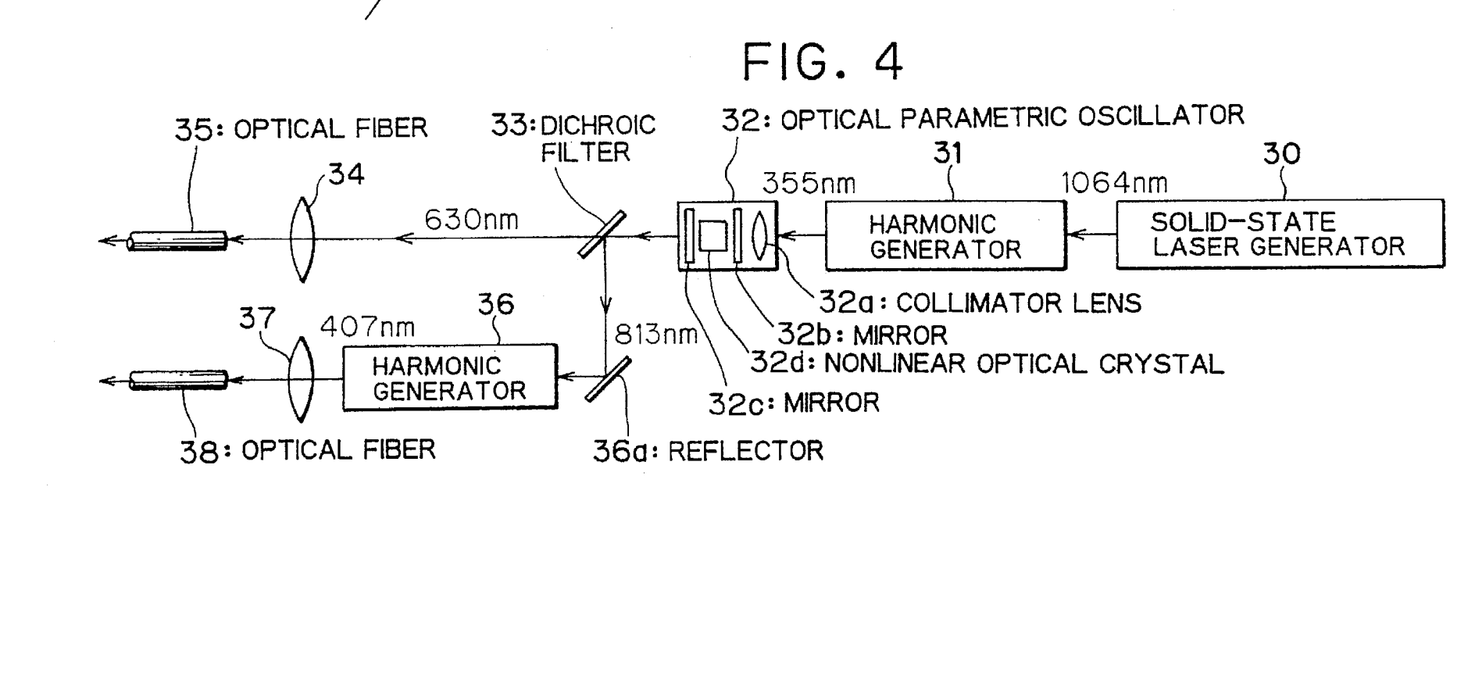
FIG. 4 shows a concrete construction of the first embodiment as shown in FIG. 3.

FIG. 4 shows a concrete construction of the laser beam generating device as shown in FIG. 3. In this embodiment, the photosensitive material and the solid-state laser generator 30 are specified to HpD and a Nd-YAG laser generator for emitting a monochromatic laser beam having a wavelength of 1064 nm, respectively. Further, the laser-wavelength varying unit 61 of this embodiment comprises a first harmonic generator 31 and an optical parametric oscillator 32. The harmonic generator 31 includes a potassium dihydrogen phosphate (KDP) crystal, and produces laser beams having higher harmonics along with a fundamental laser beam incident thereto. The optical parametric oscillator 32 includes a collimator lens 32a, two mirrors 32b and 32c and a nonlinear optical crystal such as β-BaB$_2$O$_4$ (BBO) disposed between the mirrors 32b and 32c and generates two coherent beams whose wavelengths can be varied continuously over a broad range in accordance with the change in an incident angle of a laser beam to the surface of the crystal when pumped by the incident laser beam.

An operation of producing two laser beams having different wavelengths suitable for cancer diagnosis and treatment will be described hereunder.

As shown in FIG. 4, the laser beam emitted from the Nd-YAG laser generator 30 is incident to the harmonic generator 31 to output therethrough three harmonic laser beams of 355 nm (third harmonic laser beam), 532 nm (second harmonic laser beam) and 1064 nm (fundamental laser beam). Of these laser beams, only the third harmonic laser beam of 355 nm is extracted by means of a prism (not shown). The third harmonic laser beam of 355 nm is irradiated as a pump wave to the optical parametric oscillator 32 to output two laser beams having different wavelengths (630 and 813 nm) different from the wavelength of the pump wave. As described above, the wavelengths of the output laser beams from the optical parametric oscillator 32 are variable by changing an incident angle of the pump wave to the surface of the nonlinear optical crystal. For example, when the pump wave (the laser beam of 355 nm) is incident to the optical parametric oscillator 32 in such a manner that an intersecting angle (θ) between an incident direction of the pump wave and an optical axis (C-axis) of the BBO crystal is equal to 32.7°, the output laser beams have wavelengths of 630 nm and 813 nm. The angleθ may be varied in a range of −0.5 to 0.5° in accordance with the kind of the nonlinear optical crystal.

The output laser beams from the optical parametric oscillator 32 are separated from each other through a dichroic filter 33 The laser beam of 630 nm is directly guided as a treating laser beam through a convergent lens 34 and an optical fiber 35 to the cancer focus 21a, while the laser beam of 813 nm is reflected from a reflector 36a to a second harmonic generator 36 comprising KDP crystal to output only a second harmonic laser beam (407 nm) of the incident laser beam thereto and then the laser beam of 407 nm is guided as a diagnostic laser beam through a convergent lens 37 and an optical fiber 38 to the malignant tissue 21.

Figure 5:
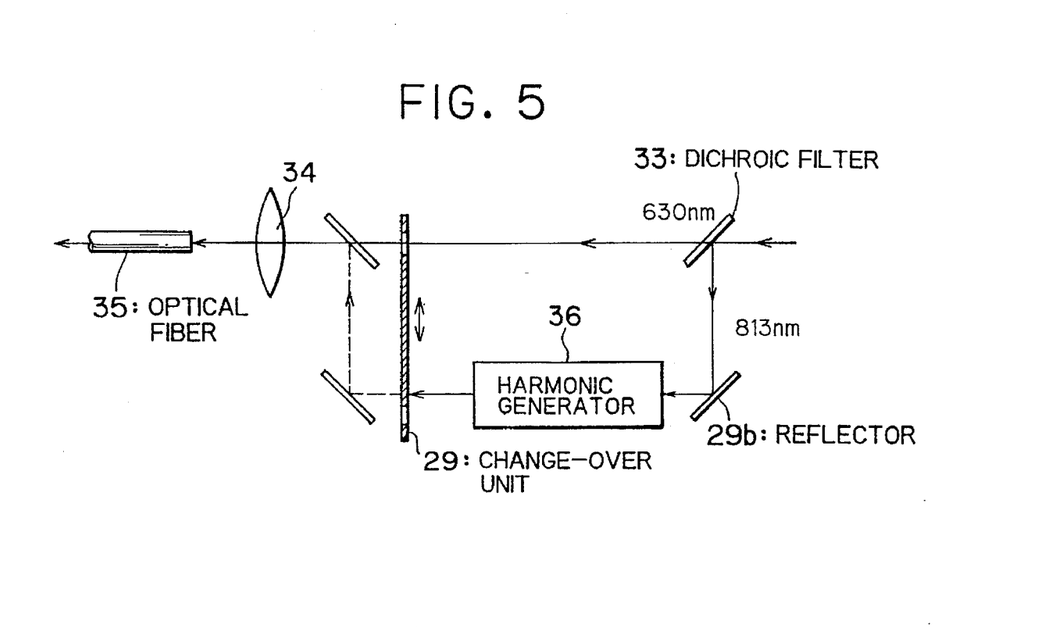
FIG. 5 shows a change-over unit used in the laser beam generating device as shown in FIG. 4.

In the above embodiment, the laser beams obtained by the optical parametric oscillator 32 are separately guided through the individual focusing lens 34 and 37 and the individual optical fibers 35 and 38, respectively. However, as shown in FIG. 5, by switching both laser beams emitted from the optical parametric oscillator 32 to each other with a change-over unit 29, these laser beams may be selectively guided through one converging lens and one optical fiber to the malignant tissue 21.

Photosensitive materials other than HpD (or DHE (dihematoporphyrin ether/ester)), such as PH-1126, NPe6, phthalocyanine and other materials, can not be used in the cancer diagnosis and treatment device of the above embodiment because the wavelength (630 nm) of the treating laser beam originated from the Nd-YAG laser generator is the absorption wavelength inherent to HpD (DHE) and the Nd-YAG laser generator generates a monochromatic laser beam which is used to produce only the laser beams of 405 nm and 630 nm for cancer diagnosis and treatment with HpD (DHE). That is, the photosensitive materials as described above have different absorption wavelengths for cancer treatment from that of HpD (DHE), and thus the photosensitive materials other than HpD (DHE) have no sensitivity to the laser beam of 630 nm. For example, the absorption wavelengths of HpD(DHE), PH-1126, NPe6 and phthalocyanine for cancer treatment are 630 nm, 650 nm, 660 nm and 680 nm, respectively. On the other hand, the absorption wavelengths of these photosensitive materials for cancer diagnosis are substantially equal to one another (405 nm). A manner of preparing HpD and chemical structures of the other photosensitive materials are described below.

(1) HpD (hematoporphyrin derivative)

This photosensitive material is prepared by dissolving hematoporphyrin hydrochloride (a mixture of twenty and several kinds of porphyrins) in a mixture of sulfuric acid and acetic acid and keeping it at pH 7.4. The absorption wavelength of this photosensitive material for cancer treatment is 630 nm. DHE (dihematoporphyrin ether/ester) is obtained by extracting only active ingredients from HpD, and has the substantially same optical characteristic as HpD.

(2) PH-1126

(3) NPe6

(4) phthalocyanine (soluble zinc phthalocyanine)

Aluminum phthalocyanine is also used as a photosensitive material having affinity to cancer, and is formed by substituting zinc metal located in the center of the above chemical structure by aluminum. This material, has the substantially same optical characteristic as zinc phthalocyanine.

As described above, the wavelength of a laser beam emitted from the solid-state laser generator of the above embodiment is fixedly set to 630 nm, and therefore only the specific photosensitive material such as HpD or DHE is used as cancer diagnosis and treatment. Accordingly, in the above embodiment, if a kind of photosensitive material is required to be changed to another kind of photosensitive material a solid-state laser generator which has been used must be exchanged to another one in order to obtain a laser beam suitable for the new photosensitive material. However, the following embodiment of the cancer diagnosis and treatment device can perform cancer diagnosis and treatment without exchanging a solid-state laser generator to another solid-state laser generator even though the kind of photosensitive material is changed.

Figure 6:
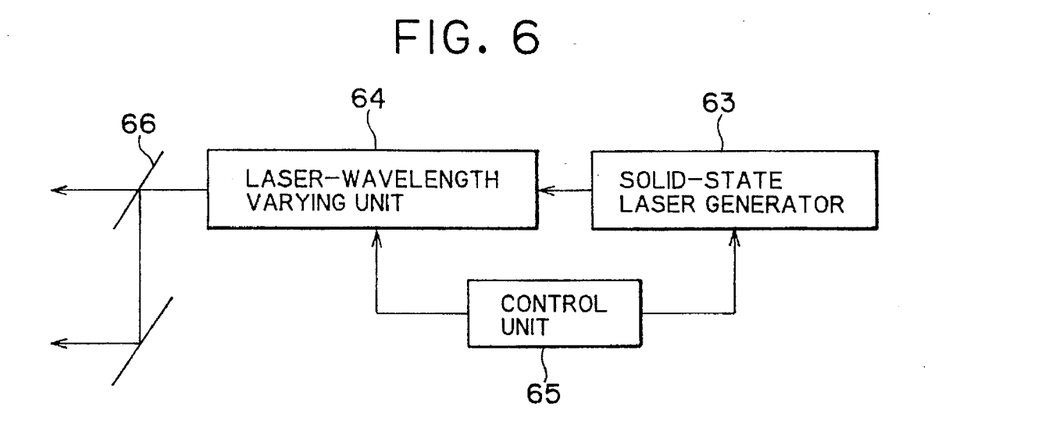
FIG. 6 shows a second embodiment of the laser beam generating device used in the cancer diagnosis and treatment device according to this invention.

FIG. 6 is a schematic view of a second embodiment of the laser beam generating device used in the cancer diagnosis and treatment device according to this invention. As shown in FIG. 6, the laser beam generating device according to this embodiment comprises a solid-state laser generator 63 capable of performing a laser oscillation in a broad wavelength range to generate a laser beam whose wavelength is variable over the broad wavelength range, a laser-wavelength varying unit 64 for converting an incident laser beam thereto to two laser beams having desired wavelengths different from that of the incident laser beam, a control unit 65 for controlling the solid-state laser generator 63 to select one of the laser beams having various wavelengths in the broad wavelength range and emit the selected laser beam to the laser-wavelength varying unit 64 and for controlling the laser-wavelength varying unit 64 to adjust an incident angle of the laser beam to the laser-wavelength varying unit 64, whereby two laser beams having desired wavelengths in accordance with the change of the wavelength of the selected laser beam are outputted from the laser-wavelength varying unit 64, and a dichroic filter 66 for separating the laser beams having the desired wavelengths, which are used for cancer diagnosis and treatment, respectively. As solid-state laser generators capable of emitting laser beams having various wavelengths in a broad wavelength range, an alexandrite ($Cr^{3+}$: $BeAl_2O_4$) laser capable of generating a laser beam having a wavelength of 700 to 830 nm, or a titanium sapphire ($Ti^{3+}$: $Al_2O_3$) laser capable of generating a laser beam having a wavelength of 680 to 900 nm may be used.

Figure 7:
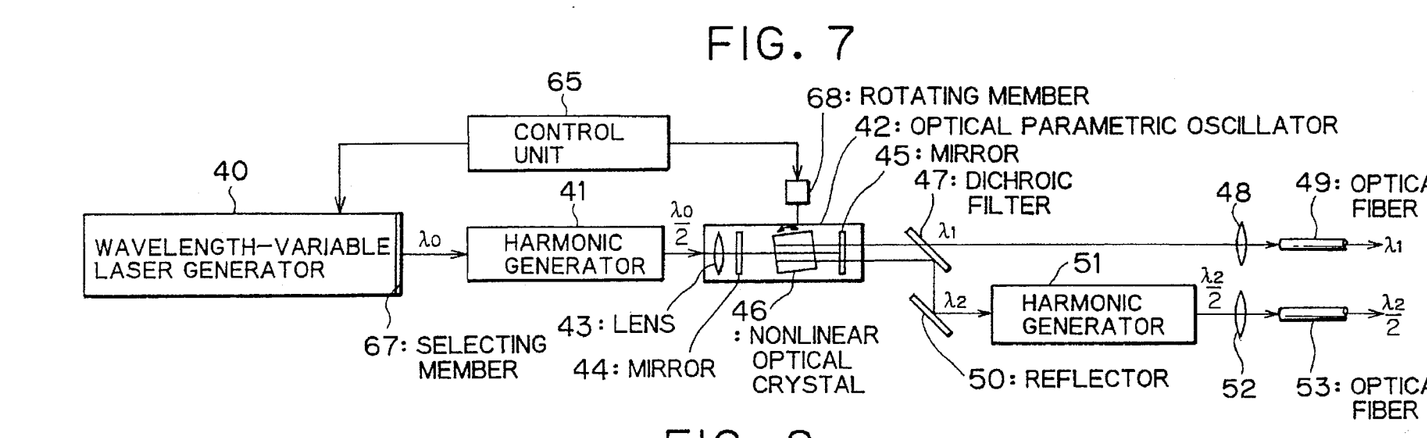
FIG. 7 shows a concrete construction of the second embodiment as shown in FIG. 6.

FIG. 7 shows a concrete construction of the laser beam generating device as shown in FIG. 6.

The laser beam generating device of this embodiment has the substantially same construction as that of FIG. 4, except that the solid-state laser generator 63 of this embodiment can generate a laser beam whose wavelength is selectively changeable in a broad range (Nd-YAG laser generates a monochromatic laser beam having a fixed wavelength) and the control unit for controlling both of the solid-state laser generator and the laser-wavelength varying unit 64 newly provided. The solid-state laser generator 40 of this embodiment includes a laser selecting member 67 such as a movable prism, by which a laser beam having a desired wavelength within the broad wavelength range is selectively outputted from the laser generator 40 to a harmonic generator 41. Like the laser beam generating device as shown in FIG. 4, the laser-wavelength varying unit 64 of this embodiment includes a first harmonic generator 41 comprising KDP crystal, and an optical parametric oscillator 42 comprising a collimator lens 43, two mirrors 44 and 45 and a nonlinear optical crystal 46 such as BBO or LBO disposed between the mirrors 44 and 45. However, unlike the laser beam generating device as shown in FIG. 4, the first harmonic generator 41 of this embodiment outputs only a second harmonic laser to the optical parametric oscillator 42, and the optical parametric oscillator 42 of this embodiment further includes a rotating member 68 such as a motor for rotating the nonlinear crystal 46 to change an incident angle of a laser beam emitted from the harmonic generator 41 to the surface of the crystal 46. The selecting member 67 and the rotating member 68 are controlled by the control unit 65 to selectively output the laser beam having the desired wavelength from the solid-state laser generator 40 and set the incident angle of the laser beam to the nonlinear optical crystal 46 to a predetermined angle. The control unit 65 comprises, for example, a mechanical member or a microcomputer to which an information on the kind of a photosensitive material to be used is inputted.

The laser beam having wavelength of $\lambda_0$ emitted from the solid-state laser generator 40 is incident to the first harmonic generator 41 to obtain a second harmonic laser beam having wavelength of $\lambda_0/2$, and then the second harmonic laser is incident to the nonlinear optical crystal 46 of the parametric oscillator 42. The nonlinear optical crystal 46 of the optical parametric oscillator 42 is rotated by the rotating member 68 to change an incident angle θ of the second harmonic laser to the crystal 46 and the optical parametric oscillator 42 outputs two laser beams having desired wavelengths of $\lambda_1$ and $\lambda_2$ on the basis of the incident second harmonic laser beam. These laser beams outputted from the optical parametric oscillator 42 are separated from each other by a dichroic filter 47. One laser beam having wavelength of $\lambda_1$ is converged through a convergent lens 48 to an optical fiber 49 and is used as a treating laser beam, while the other laser beam having wavelength of $\lambda_2$ is reflected from a reflector 50 to a second harmonic generator 51 comprising KDP crystal to obtain a second harmonic laser beam having wavelength of $\lambda_2/2$. The second harmonic laser beam thus obtained is converged through a convergent lens 52 to another optical fiber 53 and is used as a diagnostic laser beam. As described above, by switching both laser beams emitted from the optical parametric oscillator 42 to each other with a change-over unit as shown in FIG. 5, these laser beans may be selectively guided through one converging lens and one optical fiber to the malignant tissue 21.

An operation of adjusting the wavelengths of the diagnostic and treating laser beams in accordance with the kind of the photosensitive material will be described below.

The following equation shows a relationship between the wavelength ($\lambda_0/2$) of the incident laser beam to the nonlinear optical crystal 46 and the wavelengths ($\lambda_1$ and $\lambda^2$) of two laser beams outputted therefrom.

$$2/\lambda_0 = 1/\lambda_1 + 1/\lambda_2$$

As described above, it is not necessary to change the wavelength of the diagnostic laser beam ($\lambda_2/2$) in accordance with the kind of the photosensitive material to be used because the absorption wavelength of each photosensitive material for the diagnostic laser beam is broad and thus the fixed wavelength of 405 nm (or 407 nm) can be used for every photosensitive material irrespective of the kind thereof. Accordingly, the wavelength of $\lambda_2$ may be fixed in the above equation.

On the other hand, as the incident angle of the laser beam to the nonlinear optical crystal is increased, the wavelengths ($\lambda_1$ and $\lambda_2$) of the laser beams outputted from the parametric oscillator are changed in such a manner as to be approached to each other insofar as the wavelength of the incident laser beam is not changed. In addition, the relationship represented by the above equation is not changed irrespective of the change of the incident angle of the laser beam to the nonlinear optical crystal. Accordingly, if the wavelength ($\lambda_2$) of one of the output laser beams is fixed and the above equation is satisfied, in other words, if the wavelength ($\lambda_1$ of the treating laser beam is changed while the wavelength ($\lambda_2$) of the diagnostic laser beam is kept constant, as is apparent from the above equation, it is required to change the wavelength ($\lambda_0$) of the incident laser beam to the parametric oscillator 42. As described above, the wavelength of the laser beam emitted from the solid-state laser generator 40 is variable over the broad wavelength range by the selecting member 67, and thus the wavelength of the incident laser beam to the parametric oscillator 42 can be changed over the broad wavelength range (for example, $\lambda_0/2$:350 to 415 nm for the alexandrite laser generator and 340 to 450 nm for the titanium sapphire laser generator). That is, the solid-state laser beam generator used in this embodiment satisfies the above requirement.

The wavelength $\lambda_0$ of the laser beam to be selected in the solid-state laser generator 40 is determined by calculating the above equation under the condition that $\lambda_2$ is constant (that is, $\lambda_2/2$ is constantly equal to 405 nm) and $\lambda_1$ is the absorption wavelength for cancer treatment when each photosensitive material is used.

Figure 8:
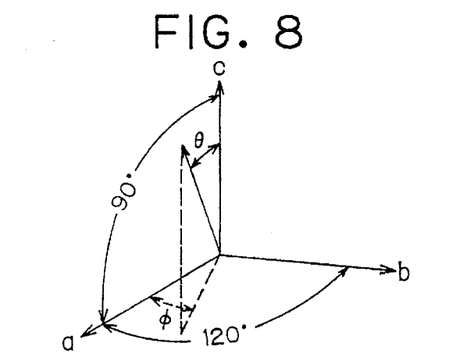
FIG. 8 is a schematic view showing a relationship between an incident direction of the laser beam to the nonlinear optical crystal axis.

Assuming that BBO crystal having a lattice constant as shown in FIG. 8 (a=b=12.532A and c=12.717A, $\alpha$=90° and $\beta$=120°) is used as the nonlinear optical crystal, the wavelength ($\lambda_0$) for each photosensitive material is obtained as follows. In the following calculation, $\theta$ and $\phi$ represent intersecting angles between the incident direction of the laser beam and the c-axis of the crystal and between the incident direction and the a-axis of the crystal, respectively, and $\phi$ is 0° when BBO crystal is used.

(1) HpD (or DHE)

$$\lambda_0 = 2 \times \lambda_1 \times \lambda_2/(\lambda_1 + \lambda_2)$$
$$= (2 \times 630 \times 810)/(630 + 810) = 709$$

Accordingly, when HpD or DHE is used as a photosensitive material, a laser beam of 709 nm is selected by the selecting member. Further, in order to obtain the output laser beams of 630 nm and 810 nm, the incident angle of the laser beam (the intersecting angle $\theta$ between the incident direction and the C-axis of the crystal) may be set to 32.7°.

(2) PH-1126

$$\lambda_0=(2\times650\times810)/(650+810)=721$$

In this case, $\theta$=32.2°

(3) NPe6

$$\lambda_0=(2\times660\times810)/(660+810)=727$$

In this case, $\theta$=31.9°

(4) Phthalocyanine $$\lambda_0=(2\times680\times810)/(680+810)=739$$

In this case, $\theta$=31.4°

The following table shows the absorption wavelengths of the above photosensitive materials to the diagnostic and treating laser beams, the incident angles of the laser beams to obtain these laser beams and the selected wavelengths of the laser beams to be emitted from the solid-state laser generator 40.

TABLE

| PHOTOSENSITIVE MATERIAL | $\lambda_0$ (nm) | $\lambda_0/2$ (nm) | $\theta$ (degree) | $\lambda_1$ (nm) | $\lambda_2$ (nm) | $\lambda_2/2$ (nm) |
|---|---|---|---|---|---|---|
| HpD (or DHE) | 709 | 354 | 32.7 | 630 | 810 | 405 |
| PH-1126 | 721 | 361 | 32.2 | 650 | 810 | 405 |
| NPe6 | 727 | 364 | 31.9 | 660 | 810 | 405 |
| phthalocyanine | 739 | 370 | 31.4 | 680 | 810 | 405 |

In the above embodiment, the wavelength of the diagnostic laser beam is constantly fixed for any photosensitive material, however, may be changed to a desired wavelength to accurately match the wavelength with a peak of absorption spectrum of the photosensitive material to be used.

As described above, according to the cancer diagnosis and treatment device having a laser beam generating device of this invention, a laser oscillation is stably carried out for a long time and it is not required to exchange laser gas to new one. Further, the wavelengths of the laser beams for cancer diagnostic and treatment can be freely changed by a simple adjustment operation of the solid-state laser generator and the laser-wavelength varying unit, and therefore any photosensitive materials can be used in the cancer diagnosis and treatment device without changing the kind of the laser beam generator even though the absorption spectra of the photosensitive materials are different. Accordingly, the diagnostic and treating procedures of cancer are smoothly and easily carried out.

What is claimed is:

1. A cancer diagnosis and treatment device for performing cancer diagnosis and treatment using a photosensitive material having affinity to cancer foci in a body and laser beams having different wavelengths in an absorption wavelength range of the photosensitive material, comprising:

a laser beam source including a solid-state laser generator for emitting a first laser beam having a first wavelength;

a laser-wavelength varying unit for converting the first laser beam into second and third laser beams, the second laser beam having a second wavelength which stimulates a sterilizing photochemical reaction between the photosensitive material and the cancer foci to perform cancer treatment, and the third laser beam having a third wavelength for inducing fluorescence inherent to the photosensitive material to enable cancer diagnosis, the first, second and third wavelengths being different from each other;

an endoscope unit for guiding the second and third laser beams from said laser-wavelength varying unit to the cancer foci and for transmitting an image of the fluorescence of the photosensitive material to an outside of the body; and a cancer observing unit having a screen for receiving the image of the fluorescence of the photosensitive material transmitted through said endoscope unit and for displaying the image on said screen to thereby perform cancer diagnosis, wherein said laser-wavelength varying unit comprises a first harmonic generator for generating higher harmonic laser beams of the first laser beam and for outputting one of the higher harmonic laser beams, and an optical parametric oscillator for receiving the one of the higher harmonic laser beams and for simultaneously generating the second and third laser beams having wavelengths suitable for the cancer treatment and diagnosis, respectively.

2. A cancer diagnosis and treatment device as claimed in claim 1, further comprising a second harmonic generator for receiving the third laser beam and for outputting a second harmonic laser beam of the third laser beam as a laser beam for the cancer diagnosis to said endoscope unit.

3. A cancer diagnosis and treatment device as claimed in claim 1, further comprising a dichroic filter for separating the second laser beam having the second wavelength and third laser beam having the third wavelength, said second and third laser beams being emitted from said laser-wavelength varying unit and applied to said dichroic filter.

4. A cancer diagnosis and treatment device as claimed in claim 1, wherein said first harmonic generator includes a potassium dihydrogen phosphate crystal.

5. A cancer diagnosis and treatment device as claimed in claim 1, further comprising a change-over unit for selectively supplying one of the second and third laser beams emitted from said laser-wavelength varying unit to said endoscope unit to perform a wavelength exchange operation for the cancer diagnosis and treatment.

6. A cancer diagnosis and treatment device as claimed in claim 1, wherein said optical parametric oscillator includes a collimator lens, two mirrors and a nonlinear optical crystal disposed between said two mirrors.

7. A cancer diagnosis and treatment device as claimed in claim 6, wherein said nonlinear optical crystal comprises a crystal selected from the group consisting of $\beta$-$BaB_2O_4$ crystal and $LiB_3O_5$ crystal.

8. A cancer diagnosis and treatment device as claimed in claim 1, wherein said solid-state laser generator comprises a monochromatic laser generator for emitting a monochromatic laser beam.

9. A cancer diagnosis and treatment device as claimed in claim 8, wherein said monochromatic laser generator comprises Nd-YAG laser for emitting a laser beam having a wavelength of 1064 nm.

10. A cancer diagnosis and treatment device for performing cancer diagnosis and treatment using a photosensitive material having affinity to cancer foci in a body and laser beams having different wavelengths in an absorption wavelength range of the photosensitive material, comprising:

a laser beam source including a solid-state laser generator for emitting a first laser beam having a first wavelength;

a laser-wavelength varying unit for converting the first laser beam into second and third laser beams, the second laser beam having a second wavelength which stimulates a sterilizing photochemical reaction between the photosensitive material and the cancer foci to perform cancer treatment, and the third laser beam having a third wavelength for inducing fluorescence inherent to the photosensitive material to enable cancer diagnosis, the first, second and third wavelengths being different from each other;

an endoscope unit for guiding the second and third laser beams from said laser-wavelength varying unit to the cancer foci and for transmitting an image of the fluorescence of the photosensitive material to an outside of the body; and a cancer observing unit having a screen for receiving the image of the fluorescence of the photosensitive material transmitted through said endoscope unit and for displaying the image on said screen to thereby perform cancer diagnosis, wherein said laser-wavelength varying unit comprises a first harmonic generator for generating higher harmonic laser beams of the first laser beam and for outputting one of the higher harmonic laser beams, and an optical parametric oscillator for receiving the one of the higher harmonic laser beams and for simultaneously generating the second and third laser beams having wavelengths suitable for the cancer treatment and diagnosis, respectively, wherein said first harmonic generator includes means for generating a first harmonic laser beam having a wavelength of 355 nm on a basis of the first laser beam and for outputting the first harmonic laser beam to said optical parametric oscillator, and said optical parametric oscillator includes means for generating the second and third laser beams having wavelengths of 630 nm and 813 nm, respectively, on the basis of the generated first harmonic laser beam.

11. A cancer diagnosis and treatment device as claimed in claim 10, further comprising a second harmonic generator for receiving the third laser beam and for outputting a second harmonic laser beam, from the received third laser beam, to said endoscope unit.

12. A cancer diagnosis and treatment device for performing cancer diagnosis and treatment using a photosensitive material having affinity to cancer foci in a body and laser beams having different wavelengths in an absorption wavelength range of the photosensitive material, comprising:

a laser beam source including a solid-state laser generator for emitting a first laser beam having a first wavelength;

a laser-wavelength varying unit for converting the first laser beam into second and third laser beams, the second laser beam having a second wavelength which stimulates a sterilizing photochemical reaction between the photosensitive material and the cancer foci to perform cancer treatment, and the third laser beam having a third wavelength for inducing fluorescence inherent to the photosensitive material to enable cancer diagnosis, the first, second and third wavelengths being different from each other;

an endoscope unit for guiding the second and third laser beams from said laser-wavelength varying unit to the cancer foci and for transmitting an image of the fluorescence of the photosensitive material to an outside of the body; and a cancer observing unit having a screen for receiving the image of the fluorescence of the photosensitive material transmitted through said endoscope unit and for displaying the image on said screen to thereby perform cancer diagnosis, wherein said laser-wavelength varying unit comprises a first harmonic generator for generating higher harmonic laser beams of the first laser beam and for outputting one of the higher harmonic laser beams, and an optical parametric oscillator for receiving the one of the higher harmonic laser beams and for simultaneously generating the second and third laser beams having wavelengths suitable for the cancer treatment and diagnosis, respectively, wherein said solid-state laser generator comprises a wavelength-variable laser generator for emitting a laser beam with a wavelength which can be varied within a predetermined wavelength range.

13. A cancer diagnosis and treatment device as claimed in claim 12, wherein said wavelength-variable laser generator comprises one of an alexandrite laser generator for emitting a laser beam having a wavelength which can be varied within a wavelength range of between approximately 700 and 830 nm, and a titanium sapphire laser generator for emitting a laser beam having a wavelength which can be varied within a wavelength range of between approximately 680 and 900 nm.

14. A cancer diagnosis and treatment device as claimed in claim 13, wherein said first harmonic generator includes means for generating a first harmonic laser beam from the first laser beam and for outputting the generated first harmonic laser beam to said optical parametric oscillator, and said optical parametric oscillator includes means for generating the second and third laser beams having variable wavelengths on the basis of the first harmonic laser beam.

15. A cancer diagnosis and treatment device as claimed in claim 14, wherein said optical parametric oscillator comprises a collimator lens, two mirrors, an nonlinear optical crystal disposed between said two mirrors and a rotating member operable for rotating said nonlinear optical crystal so as to change an incident angle of the first harmonic laser beam to said nonlinear optical crystal.

16. A cancer diagnosis and treatment device as claimed in claim 15, wherein said nonlinear optical crystal comprises a crystal selected from the group consisting of $\beta\text{-}BaB_2O_4$ crystal and $LiB_3O_5$ crystal.

17. A cancer diagnosis and treatment device as claimed in claim 15, further comprising a control unit for controlling said wavelength-variable laser generator to selectively output a laser beam having a desired wavelength within the predetermined wavelength range and for controlling said rotating member of said optical parametric oscillator to change the wavelengths of the second and third laser beams in accordance with a change of the absorption wavelength range of the photosensitive material.

* * * * *